United States Patent [19]  [11]  4,203,905
Woskow  [45]  May 20, 1980

[54] METHOD FOR PREPARING STABLE, LIQUID TETRAHYDROPHTHALIC ANHYDRIDE FOR USE IN PREPARING POLYESTERS

[75] Inventor: Marvin Z. Woskow, Houston, Tex.

[73] Assignee: Denka Chemical Corporation, Houston, Tex.

[21] Appl. No.: 934,505

[22] Filed: Aug. 17, 1978

Related U.S. Application Data

[63] Continuation-in-part of Ser. No. 541,315, Jan. 15, 1975, abandoned.

[51] Int. Cl.$^2$ ............................................. C07D 307/24
[52] U.S. Cl. ..................................... 260/346.3; 560/127
[58] Field of Search ...................... 260/346.3; 560/127

[56] References Cited

U.S. PATENT DOCUMENTS 3,431,223  3/1969  Reymore et al. ............... 560/89 X Primary Examiner—Richard Raymond
Attorney, Agent, or Firm—Kenneth H. Johnson

[57] ABSTRACT

Tetrahydrophthalic anhydride for the preparation of polyesters is conveniently prepared in a stable, liquid form for transportation and storage by adding molten anhydride to a 100° to 120° C., $C_2$ to $C_9$ glycol at rate to maintain this temperature range without raising the temperature of the mixture in increments of more than 5° F., reacting the mixture for a sufficient time to reduce the acid number of the mixture to a number in the range below the theoretical acid number for the half ester of the glycol and anhydride and 165; thereafter cooling the mixture to 155° C., adding glycol as necessary to provide a mole ratio of glycol to anhydride in the range of 1.2 to 2:1 and cooling the mixture to a temperature in the range of 40° to 70° C.

6 Claims, No Drawings

METHOD FOR PREPARING STABLE, LIQUID TETRAHYDROPHTHALIC ANHYDRIDE FOR USE IN PREPARING POLYESTERS

This application is a continuation-in-part of U.S. Ser. No. 541,315, filed Jan. 15, 1975, now abandoned.

BACKGROUND OF THE INVENTION

This invention relates to tetrahydrophthalic anhydride and a method for bulk transportation thereof for ultimate utilization in the preparation of tetrahydrophthalic anhydride-diol polyesters.

Tetrahydrophthalic anhydride (THPA) which is used in preparing high quality polyesters is normally shipped and stored in the form of flakes. The THPA flakes are normally white; however, on reheating for use in the preparation of polyesters, the material discolors. It is believed that the discoloration may be due to the formation of peroxides when the THPA is contacted with air, either during or after the formation of the flakes. Attempts to overcome this problem by maintaining the THPA in a molten state from production to use have not been successful. The THPA turns brown, apparently by decomposition, if maintained at temperatures above its melting point (e.g., above about 105° C.) for any substantial period of time, such as several days to several weeks, as would be encountered in the normal course of use.

It is an object of the present invention to provide a method of preparing tetrahydrophthalic anhydride in a form for storage and shipment, and for use in the preparation of polymers containing THPA and a diol. Another object of the present invention is to provide a method for preventing color degradation of THPA. It is an advantage of the present invention that the THPA may be maintained in liquid form at moderate temperatures and without degradation of THPA. These and other objects and advantages of the present invention will be obvious from the following discussion.

SUMMARY OF THE INVENTION

Briefly stated, the present invention is a method for preparing tetrahydrophthalic anhydride for use in the preparation of polyesters in a stable, liquid form for transportation and storage comprising admixing tetrahydrophthalic anhydride with a glycol having 2 to 9 carbon atoms, in a mol ratio of glycol to anhydride of about 0.8 to less than 1.2:1 reacting said mixture at a mixture at a temperature in the range of 120 to 170° C. for a sufficient time to reduce the acid number of said composition to below the theoretical acid number for the half ester of said glycol and said anhydride, adding sufficient glycol to said reaction mixture to make a mol ratio of glycol to anhydride in the range of 1.2 to 2:1 and recovering a liquid product, preferably having a viscosity in the range of less than 10 poise at a temperature of 50° C. The product so produced is also novel.

More particularly the method comprises the steps of:
(a) heating a glycol having 2–9 carbon atoms to a temperature in the range of 100 to 120° C.,
(b) adding molten cis-$\Delta^4$-tetrahydrophthalic anhydride to said glycol at a rate which does not cause a temperature rise in increments of more than 5° F., said temperature being maintained below 155° C., said anhydride being added to a final mole ratio of glycol to anhydride in the range of about 0.8 to 1.2:1,
(c) reacting said mixture under an inert gas blanket at a temperature in the range of 120 to 170° C. for a sufficient period of time to reduce the acid number of said composition to a number in the range below the theoretical acid number for the half ester of said glycol and tetrahydrophthalic anhydride and 165,
(d) cooling said reaction mixture to a temperature less than 155° C.,
(e) adding said glycol to said cooled reaction mixture to provide a mole ratio of glycol to anhydride in the range of 1.2 to 2:1, and
(f) cooling said mixture of glycol and reaction mixture to a temperature in the range of 40 to 70° C.

Quite clearly some half ester is formed, however, that aspect of the process is only incidental to major advantage of the invention which is the provision of THPA which is liquid at a reasonable temperature (50° C.) and which is stable, i.e., it does not crystallize on standing for relatively long periods and finally the THPA is usable for the preparation of quality polyesters. Each of the steps appear necessary for the preparation of the requisite stable, liquid THPA. Insofar as the use of the glycol-THPA material in the preparation of polyesters is concerned, the composition is the functional equivalent of THPA per se. This consideration is true to the extent that the glycol is a glycol to be employed in the polyester.

General art such as U.S. Pat. No. 3,431,223 to Reymore, Jr. et al, although dealing with the preparation of half esters has little relevance to the present invention, since it neither discloses the steps, result nor intent of the present invention.

DETAILED DESCRIPTION OF THE INVENTION

The preferred manner of carrying out the present process is to control the rate of reaction so as to not allow the temperature of the reaction of exceed 155° C. This is achieved by the addition of incremental portions, generally not exceeding 25 wt. %, of THPA to a portion of the glycol which is in the reactor or by the controlled continuous addition of THPA. In any event, addition of THPA is stopped when the reaction temperature rises more than 5° F. to allow the temperature to peak out and stabilize. The amount of glycol in the reactor is about 50 to 70% of the total glycol which will ultimately be in admixture with the THPA. In addition to the glycol and THPA a polymerization inhibitor such as hydroquinone may be present. Prior to addition of the THPA the glycol is preferably heated to about 100° to 120° C. with stirring which is continued as the molten THPA is added. Since the reaction is exothermic, heating is unnecessary. The reactants are protected with an inert gas blanket, e.g., nitrogen or $CO_2$, during the reaction and until the produce is cooled to about 50° C.

There are several isomeric forms of THPA, which have melting points ranging from 74° to 104° C. The most common form is cis-$\Delta^4$-tetrahydrophthalic anhydride which has a m.p. of 103°–4° C. in pure form.

After the total amount of THPA is added to the reactor, heating is reinstituted and continued until the acid number or reaction product is less than the theoretical of the half ester, preferably less than 250, such as for example less than about 220, which may require 1 to 1.5 hours longer (particularly at lower concentrations of glycol) of heating after completion of the acid addition.

In this step acid number would generally not be reduced to less than about 165.

Initially, some of the half-esters crystallized at temperatures between 20°-75° C. The lower ratio glycol: anhydride esters (1:1, 0.8:1) show the least tendency to crystallize, whereas the 1.5:1 esters are the worst. The 2.16 esters show an intermediate tendency. It was found that by reheating these initial half-ester samples to 150°-160° C. for a couple of hours, the tendency to crystallize at 50° and 75° C. could be eliminated. These half-esters tend to be in a super cooled state and often take a long time to begin crystallizing.

The tendency to crystallize can be greatly reduced by cooking the half-esters beyond the theoretical acid number. The 1:1 half-ester when cooked to an acid value below 220 (theoretical=262) does not crystallize at 50° C. The 1.5:1 half-ester when prepared per se at 145° to 160° C. to an acid number of 179 (theoretical=229) will still precipitate some crystals at 50° C. The amount of crystallization, however, occurring at 50° C. is reduced considerably by raising the cook temperature. A 1.5:1 half-ester which does not crystallize at 50° C. can be made by first preparing a 1:1 half-ester at 155° C. to an acid number below 220 and subsequently diluting to 1.5:1 with ethylene glycol at the end of the reaction. Any crystals developing at temperatures below 50° C. during storage will redissolve at 75° C. on reheating. IR analysis of the crystalline precipitate indicates a mixture consisting primarily of tetrahydrophthalic acid and to a lesser extent of the half-ester and the anhydride.

The balance of the glycol is added to the reaction mixture which has been cooled to a temperature of less than 155° C. and the cooling is continued to less than 100° C. Preferably, the half ester product is maintained at about 50° C. The final acid number of the product after dilution may be in the range of 155 to 220 and more preferably in the range of 165 to 195.

It should be appreciated that the reaction between glycol and acid may continue; hence, it is desirable to maintain the temperature of the product as the lowest possible temperature which will allow convenient handling. This is about 40° to 70° C., preferably no higher than 50° C. The problem with a continued reaction is a corresponding increasing in the viscosity of the half ester product, which makes the handling, i.e., pumping, pouring, etc., more difficult.

Suitable glycol include propylene glycol, ethylene glycol, triethylene glycol, tripropylene glycol, neopentyl glycol, 2,24-trimethyl-1,3-pentandiol, 2-ethyl-1,3-hexanediol and the ether glycols having 4 to 9 carbon atoms, e.g., polyethylene glycol. Particularly preferred glycols are the $C_2$ to $C_4$ glycols, preferably ethylene glycol, propylene glycol or butane glycol.

EXAMPLE 1

A THPA composition of ethylene glycol and tetrahydrophthalic anhydride (1.5:1) having an acid number of less than 185 is prepared by charging 25.30 pounds of ethylene glycol and 0.0050 pounds of hydroquinone to a stainless steel reactor. The ethylent glycol is heated to 105° C. with stirring under nitrogen. 62.0 pounds of molten THPA is added in increments of about 20%. The increment was added until the temperature of the reaction raises by 5° F. Particular care is taken not to exceed 155° C. with stirring for 1.5 hours. The reaction mixture is cooled while 12.7 pounds of ethylene glycol is added with stirring. The cooling is continued until the mixture is at 100° C. or less and the product is pumped to storage. The product is cooled to 50° C. and maintained at this temperature in storage. The product has a viscosity of 500-700 centipoise. The viscosity is about 500-700 centipoise after 40 days of storage at 50° C.

The invention claimed is:

1. A method for preparing tetrahydrophthalic anhydride for use in preparing polyesters and characterized as a stable, liquid form for transportation and storage having viscosity of less than 10 poise at a temperature of 50° C. comprising the steps of:
   (a) heating a glycol having 2 to 9 carbon atoms to a temperature in the range of 100° to 120° C.,
   (b) adding molten cis-$\Delta^4$-tetrahydrophthalic anhydride to said glycol at a rate which does not cause the temperature of the mixture to rise in increments of more than 5° F. said temperature being maintained below 155° C., said anhydride being added to a final mole ratio of glycol to anhydride in the range of about 0.8 to 1.2:1,
   (c) reacting said mixture under an inert gas blanket at a temperature in the range of 120° to 170° C. for a sufficient period of time to reduce the acid number of said mixture to a number in the range below the theoretical acid number for the half ester of said glycol and said anhydride, to not less than 165,
   (d) cooling said reaction mixture to a temperature less than 155° C.,
   (e) adding said glycol to said cooled reaction mixture to a mole ratio of glycol to anhydride in the range of 1.2 to 2:1, and
   (f) cooling said mixture of glycol and reaction mixture to a temperature in the range of 40° to 70° C.

2. The process according to claim 1 wherein the tetrahydrophthalic anhydride is added incrementally to said glycol.

3. The process according to claim 1 wherein the tetrahydrophthalic anhydride is added continuously to said glycol.

4. The process according to claim 1 wherein said glycol has 2 to 4 carbon atoms.

5. The process according to claim 4 wherein said glycol is ethylene glycol, propylene glycol or butane glycol.

6. The process according to claim 5 wherein said glycol is ethylene glycol.

* * * * *